United States Patent [19]

White

[11] 4,041,044

[45] Aug. 9, 1977

[54] PROCESS FOR THE PRODUCTION OF 2-ARYL-2H-BENZOTRIAZOLES

[75] Inventor: Howard L. White, Warwick, R.I.

[73] Assignee: Ciba-Geigy Corporation, Ardsley, N.Y.

[21] Appl. No.: 622,572

[22] Filed: Oct. 15, 1975

Related U.S. Application Data

[63] Continuation-in-part of Ser. No. 527,179, Nov. 25, 1974, abandoned.

[51] Int. Cl.² .......................................... C07D 249/20
[52] U.S. Cl. ................................................. 260/308 B
[58] Field of Search ................................... 260/308 B

[56] References Cited

U.S. PATENT DOCUMENTS 3,230,194  1/1966   Boyle .............................. 260/308 B
3,773,751  11/1973  Brooks ............................ 260/308 B Primary Examiner—Paul M. Coughlan, Jr.
Attorney, Agent, or Firm—Luther A. R. Hall

[57] ABSTRACT

An improved process for the production of 2-aryl-2H-benzotriazoles by the reduction of o-nitroazobenzene intermediates with zinc in alkaline medium comprises employing a ratio of moles of alkali to moles of o-nitroazobenzene intermediate in the range of 0.2-1.7/1 in the presence of less than 150 ppm of iron based on zinc used. The improved process results in higher yields of high purity products with a concomitant reduction in the amount of undesired cleavage amine by-products and a reduction in effluent pollution problems. The process is carried out in a polar/non-polar solvent mixture.

16 Claims, No Drawings

PROCESS FOR THE PRODUCTION OF 2-ARYL-2H-BENZOTRIAZOLES

This application is a continuation-in-part of copending application Ser. No. 527,179, filed Nov. 25, 1974, now abandoned.

BACKGROUND OF THE INVENTION

This invention pertains to a process for the preparation of 2-aryl-2H-benzotriazoles and derivatives thereof. More particularly, the invention relates to an improved process for preparing 2-aryl-2H-benzotriazoles whereby high yields of the desired products are obtained and effluent pollution problems occurring with present processes for making such products are greatly reduced.

The known chemical and electrolytic reduction processes for preparing 2-aryl-benzotriazoles are not practical or economically attractive in many cases. The widely used zinc dust and sodium hydroxide system can produce effluent pollution problems in respect to waste disposal of zinc sludge which is of increasing environmental concern.

It is therefore an object of this invention to provide an improved process for the preparation of 2-aryl2H-benzotriazoles mitigating severe pollution and environmental problems.

A further object of this invention is to prepare 2-aryl-2H-benzotriazoles by reducing and cyclizing the corresponding o-nitroazobenzene under certain conditions hereinafter set forth in greater detail whereby high yields of the products can be obtained in acceptable purity.

The 2-aryl-2H-benzotriazoles have found wide use as dyestuff intermediates, optical brightener blue fluorescent agents and selective ultraviolet light absorbing stabilizers affording valuable protection for fibers, films and a variety of polymeric structures subject to deterioration by ultraviolet radiation. These materials have become important items of commerce.

The 2-aryl-2H-benzotriazoles are complex organic molecules which require careful synthetic procedures for their production in good yield and purity.

These materials can be prepared by a variety of methods, but most conveniently by either Process I, the oxidation of o-aminoazobenzene intermediates, or Process II, the reduction of o-nitroazobenzene intermediates. Process I:

The oxidation of o-aminoazobenzene intermediates proceeds schematically as seen in Equation A

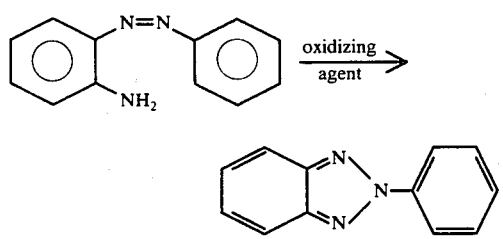

(A)

where oxidizing agents such as sodium hypochlorite, ammoniacal copper sulfate, air in aqueous or aqueous-pyridine solution, hydrogen peroxide, hexavalent chromium compounds, potassium permanganate and the like may be used. This process is described in U.S. Pat. Nos. 2,362,988, 2,784,183, 3,055,896 and 3,072,585. Process II:

The reduction of o-nitroazobenzene intermediates proceeds schematically as seen in Equation B where a variety of reducing agents

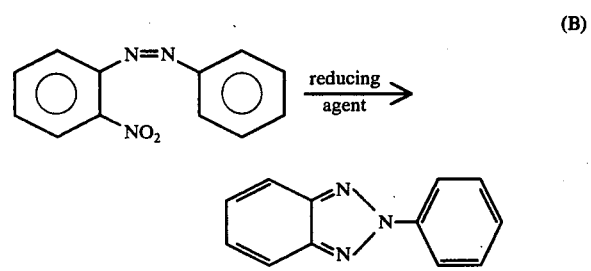

(B)

may be employed as seen from the teachings of U.S. Pat. No. 2,362,988. These include alkali sulfides, zinc and ammonia at 80°-100° C, sodium hydrosulfide, zinc and hydrochloric acid and ammonium sulfide. The use of ammonium sulfide was also reported by S. N. Chakrabarty et al, *J. Indian Chem. Soc.*, 5, 55 (1928); CA, 23, 836 (1929) with mixed results depending on the presence or absence of substituent groups on the 2-aryl group. In some cases the desired 2-aryl-2H-benzotriazole was not formed at all with the product of the reduction being only an aromatic amine.

Electrolytic reduction of o-nitroazobenzene intermediates was reported by H. Itomi, *Mem Coll. Sci. Kyoto Imp. Univ.*, 12A, No. 6, 343 (1929); CA, 24, 2060 (1930) with the use of a copper cathode in dilute sodium hydroxide solution. Yields varied from 25 to 60% depending on specific embodiments and conditions, but with a major impurity being formed, namely the corresponding o-aminoazobenzene by-product.

The use of zinc dust and sodium hydroxide as the reducing system for the o-nitroazobenzene intermediates was reported by K. Elbs et al, *J. Prakt Chem.*, 108, 209 (1924); CA, 19, 514 (1925). The yields reported varied from 30 to 85% depending on the specific o-nitroazobenzene intermediates involved.

U.S. Pat. Nos. 3,055,896 and 3,072,585 also teach the use of zinc dust and sodium hydroxide as the reducing system for o-nitroazobenzene intermediates. In these cases large molar ratios of sodium hydroxide to the o-nitroazobenzene intermediates (6–20 to 1) are taught. The yield and purity of products are not taught, but further recrystallization is indicated as necessary to obtain products of good purity.

U.S. Pat. Nos. 3,230,194 and 3,773,751 also teach the use of large molar ratios of sodium hydroxide to the o-nitroazobenzene intermediate namely 6.7 to 1 and 4.4 to 1 respectively. Recrystallization is indicated as necessary to obtain a pure product.

DETAILS OF THE DISCLOSURE

This invention relates to an improved process for the preparation of 2-aryl-2H-benzotriazoles by the reduction of o-nitroazobenzene intermediates with zinc in alkaline medium wherein the improvement comprises employing a ratio of moles of alkali to moles of o-nitroazobenzene intermediate in the range of 0.2–0.8/1 for one type of o-nitroazobenzene and in the range of 1.2–1.7/1 for a second type of o-nitroazobenzene in the presence of a total amount of iron impurities in the reaction system of less than 150 ppm based on zinc used.

The improved process results in higher yields (from 68–70% to 77–78%) of high purity 2-aryl-2H-benzotriazole product as a first crop with high yields (5–11%) of a second crop material of quality only slightly less pure than the first crop. There is a concomitant reduction in the amount of undesired cleavage amine by-products. The latter represents both an economic penalty in manufacture of the desired 2-aryl-2H-benzotriazole products and a source of effluent pollution problems. Much less acid is needed to remove the amine by-products from the 2-aryl-2H-benzotriazole products in the improved process reducing the volume and severity of the effluent problem involved.

More specifically, the instant invention provides an improved process for productuion of 2-aryl-2H-benzotriazole compounds having the formula I

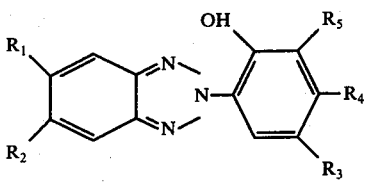

(I)

wherein
$R_1$ is hydrogen or chlorine,
$R_2$ is hydrogen, chlorine, lower alkyl of 1 to 4 carbon atoms, lower alkoxy of 1 to 4 carbon atoms, carboalkoxy of 2 to 9 carbon atoms, carboxy or $-SO_3H$,
$R_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
$R_4$ is hydrogen, lower alkyl of 1 to 4 carbon atoms, alkoxy of 1 to 8 carbon atoms, chlorine or hydroxyl, and
$R_5$ hydrogen, alkyl of 1 to 12 carbon atoms, chlorine, cycloalkyl of 5 to 6 carbon atoms or phenylalkyl of 7 to 9 carbon atoms.

$R_2$ can be lower alkyl of 1 to 4 carbon atoms such as methyl, ethyl or n-butyl. $R_2$ can also be lower alkoxy of 1 to 4 carbon atoms such as methoxy, ethoxy or n-butoxy. $R_2$ can also be carboalkoxy of 2 to 9 carbon atoms such as carbomethoxy, carboethoxy, or carbo-n-octoxy.

$R_3$ can be alkyl of 1 to 12 carbon atoms such as methyl, ethyl, sec-butyl, tert-butyl, tert-amyl, tert-octyl or n-dodecyl. $R_3$ can also be alkoxy of 1 to 4 carbon atoms such as methoxy, ethoxy or n-butoxy. $R_3$ is also phenyl substituted with alkyl groups, said alkyl groups having 1 to 8 carbon atoms such as methyl, tert-butyl, tert-amyl or tert-octyl. $R_3$ can also be cycloalkyl of 5 to 6 carbon atoms such as cyclopentyl or cyclohexyl. $R_3$ is also carboalkoxy of 2 to 9 carbon atoms such as carbomethoxy, carboethoxy, carbo-n-butoxy or carbo-n-octoxy. $R_3$ is also phenylalkyl of 7 to 9 carbon atoms such as benzyl, α-methylbenzyl or α,α-dimethylbenzyl.

$R_4$ can be lower alkyl of 1 to 4 carbon atoms such as methyl, ethyl or n-butyl.

$R_4$ can also be alkoxy of 1 to 8 carbon atoms such as methoxy, ethoxy, n-butyloxy or octyloxy.

$R_5$ can be lower alkyl of 1 to 8 carbon atoms such as methyl, sec-butyl, tert-butyl, tert-amyl or tertoctyl.

$R_5$ can also be cycloalkyl or 5 to 6 carbon atoms such as cyclopentyl or cyclohexyl. $R_5$ is also phenylalkyl of 7 to 9 carbon atoms such as benzyl, α-methylbenzyl or α,α-dimethylbenzyl.

Preferably $R_1$ is hydrogen.
Preferably $R_2$ is hydrogen, chlorine, lower alkyl of 1 to 2 carbon atoms, methoxy or carboxy.
Preferably $R_3$ is alkyl of 1 to 8 carbon atoms cyclohexyl, phenyl, chlorine, α-methylbenzyl or carboxyethyl.
Preferably $R_4$ is hydrogen, hydroxyl, methyl or alkoxy of 1 to 8 carbon atoms.
Preferably $R_5$ is hydrogen, chlorine, alkyl of 1 to 8 carbon atoms, cyclohexyl, benzyl or α-methylbenzyl.
Most preferably $R_2$ is hydrogen or chlorine.
Most preferably $R_3$ is methyl, tert-butyl, tertamyl, tert-octyl, sec-butyl, cyclohexyl, chlorine or carboxyethyl.
Most preferably $R_4$ is hydrogen.
Most preferably $R_5$ is hydrogen, chlorine, methyl, sec-butyl, tert-butyl, tert-amyl, tert-octyl or α-methylbenzyl.

The process involved the reduction of an o-nitroazobenzene intermediate of the formula II

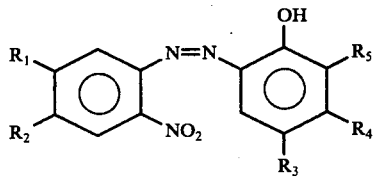

II wherein $R_1$, $R_2$, $R_3$, $R_4$ and $R_5$ are described previously.

The o-nitroazobenzene intermediates of formula II useful in this improved process fall into two general types, Type 1 and Type 2.

In Type 1, $R_5$ cannot be hydrogen and there must be a substituent in the position ortho to the hydroxy group.

In Type 2, $R_5$ must be hydrogen and the hydroxy group must not have a substituent in the ortho position thereto.

The Type 1 o-nitrobenzene intermediates normally do not form soluble alkali metal phenolate salts, especially when the $R_5$ group is a large hydrocarbon residue. For apparent steric and possibly other unknown reasons, the hydroxy group appears to be inaccessible to or relatively unreactive with the aqueous alkali, thus making even a low molar amount of alkali available for producing the reducing couple with zinc.

The Type 2 o-nitroazobenzene intermediates, however, do form soluble or insoluble alkali metal phenolate salts requiring one mole of alkali per mole of hydroxy group (or o-nitroazobenzene intermediate) in the process.

Thus, the classification of the intermediates of formula II into Type 1 or 2 depends not on solubility of the phenolate salt, but rather on the presence or absence of substitution ortho to the hydroxyl group.

The reasons for the striking differences in the alkali requirement for the successful reduction of an o-nitroazobenzene intermediate of Type 1 compared to one of Type 2 are not clearly understood. With Type 1 intermediates, a molar ratio of alkali to o-nitroazobenzene intermediate in the range of 0.2–0.8/1 is needed. With Type 2 intermediates, a molar ratio of alkali to o-nitroazobenzene intermediate in the range of 1.2–1.7/1 is required.

In the absence of ortho substitution to the hydroxyl group of Type 2 intermediates, apparently 1 mole of alkali per mole of intermediate is required to form the phenolate salt and then an additional 0.2 mole/mole of intermediate is needed to produce a reducing couple with zinc.

It is contemplated that with zinc in sodium hydroxide solution two different reducing couples can exist as seen in v. R. Scholder et al, *Z. Anorg Allg. Chem.*, 241, 76 (1939) as $$Zn + 3(OH)^- \rightarrow Zn(OH)_3^- + 2e \qquad 2.$$

$$Zn + 4(OH)^- \rightarrow Zn(OH)_4^- + 2e. \qquad 2.$$

The improved process using low concentrations of alkali corresponds to the first couple which appears to be a less powerful, milder, apparently more specific reducing system.

It is further contemplated that with the Type 1 intermediates less alkali can react with the hydroxyl group present for steric and related considerations thus requiring less total alkali to produce the mild reducing couple described above.

In the case of the Type 2 intermediates, one mole of alkali is consumed by reaction with the hydroxyl group present. Only an additional 0.2 moles of alkali is then needed to produce the mild reducing couple described above.

With the o-nitroazobenzene intermediates of Type 1, the improved process involves the cyclic reduction of the o-nitroazobenzene intermediate of formula II wherein $R_5$ is alkyl of 1 to 12 carbon atoms, chlorine, cycloalkyl of 5 to 6 carbon atoms or arylalkyl of 7 to 9 carbon atoms with zinc in an aqueous alkali metal hydroxide medium wherein the improvement comprises employing a ratio of moles of alkali to moles of o-nitroazobenzene intermediate in the range of 0.2–0.8/1, preferably 0.3–0.7/1, most preferably 0.3–0.6/1, in the presence of a total amount of the iron impurities in the reaction system of less than 150 ppm based on zinc used, preferably of less than 100 ppm and most preferably of less than 50 ppm. With Type 1 intermediates, preferably $R_5$ is chlorine, alkyl of 1 to 8 carbon atoms, cyclohexyl, benzyl or α-methylbenzyl and most preferably $R_5$ is chlorine, methyl, sec-butyl, tert-butyl, tert-amyl, tert-octyl and α-methylbenzyl.

With the o-nitroazobenzene intermediates of Type 2, the improved process involves the cyclic reduction of the o-nitroazobenzene intermediate of formula II wherein $R_5$ is hydrogen with zinc in an aqueous alkali metal hydroxide medium wherein the improvement comprises employing a ratio of moles of alkali to moles of o-nitroazobenzene intermediate in the range of 1.2 to 1.7/1, preferably 1.2 to 1.4/1, most preferably 1.2 to 1.3/1, in the presence of a total amount of iron impurities in the reaction system of less than 150 ppm based on zinc used, preferably of less than 100 ppm and most preferably of less than 50 ppm.

The definitions of $R_1$, $R_2$, $R_3$ and $R_4$ are as previously set forth and are the same for both Type 1 and Type 2 o-nitroazobenzene intermediates.

The starting o-nitroazobenzene intermediates are prepared by coupling the appropriate o-nitrobenzenediazonium compounds of formula III

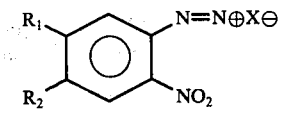

III wherein $R_1$ and $R_2$ are as described previously and X is chloride, sulfate, or other anionic species, but preferably chloride, with phenols of formula IV

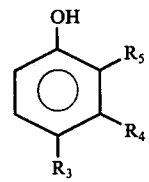

IV which couple in the ortho position to the hydroxy group.

The o-nitrobenzenediazonium compounds are in turn prepared by standard diazotization procedures using sodium nitrite in acid solution with the corresponding o-nitroanilines of formula V

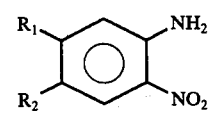

V

For illustration purposes some specific examples of compounds of formulas IV and V are listed. These items are generally available as items of commerce.

COMPOUNDS OF FORMULA IV p-cresol
2,4-di-tert-butylphenol
2,4-di-tert-amylphenol
2,4-di-tert-octylphenol
2-tert-butyl-4-methylphenol
4-cyclohexylphenol
4-tert-butylphenol
4-tert-amylphenol
4-tert-octylphenol
2,4-dimethylphenol
3,4-dimethylphenol
4-chlorophenol
2,4-dichlorophenol
3,4-dichlorophenol
4-phenylphenol
4-phenoxyphenol
3-octyloxyphenol
4-o-tolylphenol
4-(4'-tert-octyl)phenylphenol
ethyl 4-hydroxybenzoate
n-octyl 4-hydroxybenzoate
4-methoxyphenol
4-n-octylphenol
4-n-dodecylphenol
resorcinol
4-(α-methylbenzyl)phenol
2-(α-methylbenzyl)-4-methylphenol
2-cyclohexyl-4-methylphenol
4-sec-butylphenol
2-sec-butyl-4-tert-butylphenol 2-tert-butyl-4-sec-butylphenol
4-carboxyethylphenol
2-methyl-4-carboxyethylphenol.

Preferably compounds of formula IV useful in this invention are
p-cresol
2,4-di-tert-butylphenol
2,4-di-tert-amylphenol
2,4-di-tert-octylphenol
2-tert-butyl-4-methylphenol
4-tert-octylphenol
4-n-octylphenol
4-n-dodecylphenol
resorcinol
2-sec-butyl-4-tert-butylphenol
2-(α-methylbenzyl)-4-methylphenol
3-octyloxyphenol

COMPOUNDS OF FORMULA V o-nitroaniline
4-chloro-2-nitroaniline
4,5-dichloro-2-nitroaniline
4-methoxy-2-nitroaniline
4-methyl-2-nitroaniline
4-ethyl-2-nitroaniline
n-butyl 3-nitro-4-aminobenzoate
n-octyl 3-nitro-4-aminobenzoate
4-n-butoxy-2-nitroaniline
3-nitro-4-aminobenzoic acid
3-nitro-4-aminobenzenesulfonic acid.

Preferably compounds of Formula V useful in this invention are
o-nitroaniline
4-chloro-2-nitroaniline.

The process is carried out in an aqueous/organic solvent medium where the exact choice of organic solvent is determined by the solubility characteristics of the specific o-nitroazobenzene intermediates and 2-aryl-2H-benzotriazle products involved.

In the case of the Type 1 o-nitroazobenzene intermediates, the use of aqueous alkali and the polar/non-polar solvent mixture, isopropanol/Amsco mineral spirits, proved beneficial in order to provide the best ambience for the rapid reduction of the o-nitroazobenzene intermediate (Type 1). The use of a single organic solvent either isopropanol or Amsco mineral spirits alone with aqueous alkali required a much longer reaction time to effect the reduction of the o-nitroazobenzene intermediate to the corresponding 2-aryl-2H-benzotriazole.

The polar materials which may be used in the mixed solvent for the instant process include isopropanol, ethanol, methanol, n-butanol, 2-ethylhexanol and the like. Isopropanol is preferred. The non-polar materials useful in the mixed solvents are Amsco mineral spirits, toluene, benzene, hexane, cyclohexane, xylene, heptane and the like. Amsco mineral spirits are preferred.

The ratio of weight of polar to non-polar materials in the solvent mixture is about 2/1 to 2/3, and preferably 3/2 to 1/1.

In the case of Type 2 o-nitroazobenzene intermediates the same solvent mixtures used with the Type 1 intermediates can be used, but an aqueous alkali/aromatic solvent mixture proved particularly beneficial in the instant process with the Type 2 o-nitroazobenzene intermediate reductions. The aromatic solvents included benzene, toluene and xylene with toluene being preferred.

The alkaline medium used in this improved process is an aqueous alkali metal hydroxide solution. The alkali metal hydroxides used in this improved process are sodium hydroxide, potassium hydroxide and lithium hydroxide. For reasons of economy and availability, sodium hydroxide is preferred.

Contemplated equivalents for the alkali metal hydroxides include ammonia and the alkaline earth hydroxides such as magnesium hydroxide, calcium hydroxide and barium hydroxide.

Although the decrease in molar ratio of alkali to the o-nitroazobenzene intermediates raises the yields of the desired 2-aryl-2H-benzotriazoles significantly, the yields are further enhanced when the total concentration of iron impurities in the reaction system is kept to low levels (under 150 ppm based on zinc used).

It is suprising that the low alkali concentration increases the yield of desired product on the reduction step. It is also surprising that the decrease of the iron concentration further increases the yield of the 2-aryl-2H-benzotriazoles.

In Table I are seen the results on yields of the effect of the molar ratio of alkali to o-nitroazobenzene intermediate, (Type 1), at a low and constant concentration of iron impurities, on reaction time required to achieve complete reduction, the exotherm experienced as zinc was added all at one time to the system and the amount of undesirable aminophenol cleavage by-product formed.

A comparison with a typical run at a high ratio of alkali to o-nitroazobenzene intermediate (Type 1) is also shown. At ratios above 0.9 moles alkali to 1 mole o-nitroazobenzene intermediate (Type 1), extreme exotherms are noted with each addition of zinc to the system requiring expensive brine cooling, rather than simple water cooling, to keep the reaction temperature within the controlled limits (55° to 65° C). Reaction times at 65° are not appreciably less than when less alkali is used, but the total yield of desired 2-aryl-2H-benzotriazole is considerably less (71.8% compared to 81.5%, see Example 1) and the yield of undesirable cleavage amine by-product is many times as great (11.4% compared to 2–3%, see Example 1). With less undesired by-product, the quality of the desired product is concomitantly better making product isolation and purification by one crystallization and trituration correspondingly simplified.

TABLE I

Effect of Molar Ratio of Alkali to o-Nitroazobenzene Intermediate (Type 1) at Low and Constant Iron Content on Reduction to 2-Aryl-2H-Benzotriazole

| Mole Alkali to o-Nitroazobenzene Intermediate (1 mole) | 0.212 | 0.318 | 0.605 | 0.848 | 1.67* |
|---|---|---|---|---|---|
| Exotherm when Zn is added at 55° C with Air-cooling | small ca.1° C | small ca.1° C | moderate ca.7° C | strong | very strong |
| Hold Time at 65° C to Complete Reduction (hours) | 7.25 | 5.25 | 2.75 | 1.5 | 1.5 |
| First Crop Yield % | 79.5 | 80.4 | 80.7 | 76.7 | 71.5 |
| By-Product Material Precipitated at pH 5.5 Calculated as Mole % Aminophenol Hydrochloride | 3 | 2–3 | 5.5 | 8.5 | 11.4 |

*Zinc added portionwise

As seen from Table I, the mole ratio of alkali to o-nitroazobenzene intermediate (Type 1) in the improved process can range from about 2 to 0.8/1. Preferably the ratio is 0.3 to 0.7/1 in order to optimize time of reaction, product yields and the like, and most preferably the ratio is 0.3 to 0.6/1.

When the mole ratio of alkali to o-nitroazobenzene intermediate of Type 2 is in the operable range for the improved process described above for the Type 1 intermediates, the desired 2-aryl-2H-benzotriazoles derived from the Type 2 intermediates are not formed in acceptable yield and purity.

However, it is seen on Table II, when the moles of sodium hydroxide to moles of o-nitroazobenzene intermediate of Type 2 were increased to over 1.2/1, that the reduction to the desired 2-aryl-2H-benzotriazole occured readily, but that the reduction was not totally specific and that the desired product was contaminated with byproducts, largely of amine nature.

It is contemplated that the lack of specificity seen in the results on Table II may be related to the concentration of the o-nitroazobenzene intermediate in the reduction phase. In the water/isopropanol/Amsco mineral spirits system employed, it is considered that the reduction phase is the aqueous alkali/isopropanol phase rather than the organic phase Amsco mineral spirits-/isopropanol.

TABLE II
Effect of Molar Ratio of Sodium Hydroxide to o-Nitroazobenzene Intermediate of Type 2 at Low and Constant Iron Content on Reduction to 2-Aryl-2H-Benzotriazole

| Run | Moles of Sodium Hydroxide to o-Nitroazobenzene Intermediate of Type 2 (1 mole) | Reaction Time in Hours at 65° C | Reaction Results as Seen by TLC Analysis of Reaction Mixture* |
|---|---|---|---|
| 1 | 0.42 | 13 | Essentially no reduction, trace of N-oxide seen |
| 2 | 0.60 | 5 | Essentially no reduction, low concentration of N-oxide seen |
| 3 | 0.84 | 5 | Mixture of starting material and N-oxide |
| 4 | 1.26 | 5 | No starting material or N-oxide present, reduction occurred to desired product plus by-products |
| 5 | 1.68 | 5 | No starting material or N-oxide present, reduction occurred to desired product plus by-products |

*Solvent was isopropanol/Amsco mineral spirits/water.

Accordingly, the isopropanol/Amsco mineral spirits were replaced by toluene. The reduction occurs in the aqueous caustic phase and the desired product is concentrated in the toluene phase. Additionally, the toluene phase can be saturated at lower temperatures with premade product allowing for an increased recovery of desired product upon final crystallization from the toluene. A convenient method of achieving this is to reuse the mother liquor from a previous run, already saturated with desired product, in a subsequent reduction batch reaction.

On Table III is seen the results of reactions carried out in toluene/aqueous alkali systems, at various ratios of alkali to o-nitroazobenzene intermediates of Type 2. The specificity of the reduction reaction to give the desired 2-aryl-2H-benzotriazole with a mininum of by-products was greatly increased in this aqueous toluene system.

TABLE III
Effect of Molar Ratio of Sodium Hydroxide to o-Nitroazobenzene Intermediate of Type 2 in Toluene/Water at 65° C

| Run | Moles of Sodium Hydroxide to o-Nitroazobenzene Intermediate of Type 2 (1 mole) | Reaction Time in Hours | Reaction Results by TLC Analysis | Yield of Product Isolated | In Mother Liquor | Total |
|---|---|---|---|---|---|---|
| 1 | 0.84 | 16 | Mixture product, N-oxide and starting material | Not isolated | | |
| 2 | 0.84 | 20+ 8 at 80° C | N-oxide, product and by-products | Not isolated | | |
| 3 | 1.26 | 7 | Trace N-oxide | 48.9 | 39.1 | 88.0 |
| 4 | 1.26 | 4 | No N-oxide | 57.0 | 29.6 | 86.6 |
| 5 | 1.40 | 4 | Trace N-oxide | 61.0 | 17.9 | 78.9 |
| 6 | 1.6 | 4 | Trace N-oxide | 61.1 | 20.4 | 81.5 |
| 7 | 1.26* | 3.5 | Trace N-oxide | 78.4 | 2.4 | 80.8 |
| 8 | 3.37* | 0.5 | No N-oxide | 73.3 | 4.5 | 77.8 |

*The solubility of the desired product was decreased in the toluene when using toluene saturated with premade product thus, increasing significantly the isolated yields in these runs.

A comparison of Run 7 on Table III shows that the use of the 1.26 moles of sodium hydroxide to 1 mole of o-nitroazobenzene of Type 2 led to a commercially significant 5% increase in isolated yield of pure product compared to Run 8 where a high amount of alkali (3.37/1) was used.

In commercial processes, an increase in yield of 5% can be very significant, both in reducing unit costs, reducing effluent and pollution problems as well as after resulting in a purer product since by-product formation is concomitantly depressed.

In the presence of iron, the yields of desired 2-aryl-2H-benzotriazoles fall off even when the molar ratio of alkali to o-nitroazo intermediate is low and the amount of cleavage amine by-products greatly increased. In Table IV, the effect of adding iron as iron oxide (Fe₂O₃) even at the parts per million (ppm) levels based on the charge of zinc is seen. The yield of desired products is greatly affected. At the 210 ppm level, the yield drops nearly 15% to 67.6% compared to 82.4% control. Addition of more iron impurities produces even more deleterious results with a greatly enhanced yield of undesired by-products.

TABLE IV

Effect of Iron Added as Ferric Oxide on Reduction of o-Nitroazobenzene Intermediate (Type 1) at a Constant Ratio of Alkali (0.42 mole) to o-Nitroazobenzene Intermediate (1 mole)

| ppm Fe on Zn used | 2100 | 700 | 210 | 40 | none |
|---|---|---|---|---|---|
| Time Required at 65° for Complete Reduction (hours) | * | 7.5 | 5 | 4–5 | 3.75 |
| First Crop Yield % | * | 48.6 | 67.6 | 80.5 | 82.4 |
| By-Product material Precipitated at pH 5.5 Calculated as Mole % Aminophenol Hydrochloride | — | 31.2 | 17.0 | 2.5 | 4.7 |

*Reduction was incomplete and the product formed is the N-oxy compound corresponding to the o-nitroazobenzene intermediate The addition of iron impurities as ferric chloride as seen on Table V is even more pronounced. Only 80 ppm of iron based on the zinc charged leads to low yields (66.5%) of the desired 2-aryl-2H-benzotriazole product.

TABLE V

Effect of Iron Added as Ferric Chloride on Reduction o-Nitroazobenzene Intermediate (Type 1) at a Constant Ratio of Alkali (0.42 mole) to o-Nitroazobenzene Intermediate (1 mole)

| ppm Fe on Zn used | 80 | 130 |
|---|---|---|
| First Crop Yield % | 66.5 | 59.1 |
| By-Product Material Precipitated at pH 5.5 Calculated as Mole % Aminophenol Hydrochloride | 18.5 | 23.1 |

Commercial zinc dust varies widely in the amount of residual iron impurities ranging from under 100 ppm to over 1500 ppm iron. The latter zinc dusts are totally unacceptable for use with this improved process due to their high iron impurity contents. Zinc dust containing 100 ppm or less iron can be used satisfactorily in the improved process. Preferably the iron content in the zinc dust should be less than 80 ppm and most preferably less than 50 ppm.

The physical state of the iron is also apparently critical. The more finely divided ferric oxide resulting from addition of ferric chloride to the alkaline reduction system proved particularly detrimental compared to the addition of commercial preformed ferric oxide. The use of more finely divided ferric oxide required iron levels in the 50 ppm range or less for satisfactory results.

Iron can also be introduced into the system from sources other than the zinc dust. Another source of iron present during the reduction step can be the o-nitrozaobenzene intermediate itself. This intermediate is prepared by the coupling of an appropriate o-nitroaryl diazonium compound of formula III with an appropriate phenol of formula IV in an acidic or alkaline aqueous medium. If the o-nitroazobenzene intermediate is coupled in acid medium and then is not carefully washed with water after its preparation to remove all traces of acid, the o-nitroazobenzene intermediate on storage may become contaminated with traces of iron caused by the corrosive action of residual acid on the steel storage drums used to store the intermediate prior to its later reduction to the 2-aryl-2H-benzotriazole.

On Table VI the effect of residual iron impurities arising from the o-nitroazobenzene intermediate on product yields are listed. It has been found that such adventitious iron impurties can be removed from the o-nitroazobenzene intermediate conveniently by an aqueous acid reslurry prior to the low alkali reduction process of this invention.

TABLE VI

Effect of Iron Present from Earlier Preparation o-Nitroazobenzene Intermediate on the Subsequent Reduction* of the o-Nitroazobenzene Intermediate (Type 1) at Constant Ratio of Alkali (0.42 moles) to o-Nitroazobenzene Intermediate (1 mole)

| ppm Fe from o-Nitroazobenzene Intermediate | 200–400 | <35 | <35 | <35 |
|---|---|---|---|---|
| First Crop Yield % on Reduction to 2-aryl-2H-Benzotriazole | 62 | 80.7 | 79 | 83 |

*Zinc used had "no" iron present. See Table IV column with "none" for iron content. ppm Fe is based on zinc used.

It is seen from Tables IV-VI that it is the total concentration of iron impurities in the reaction system which determines the course of the reaction, and the yield and purity of the desired products regardless of the original source of the iron contamination. The chief sources of iron contamination are the zinc dust and the o-nitroazobenzene intermediate.

From a practical point of view the iron impurity content of the zinc dust used in this process should never exceed 100 ppm, preferably not exceed 80 ppm and most preferably be under 50 ppm.

Likewise, the iron impurity content of the o-nitroazobenzene intermediate should not exceed 50 ppm (calculated on zinc to be used), preferably not to exceed 35 ppm and most preferably be under 10 ppm.

With these guidelines, the process of this invention is carried out in the presence of a total amount of iron impurities in the reaction system of less than 150 ppm based on zinc used, preferably less than 100 ppm based on zinc used and most preferably less than 50 ppm based on zinc used.

During the coupling step of an appropriate o-nitroaryl diazonium compound of formula III with an appropriate phenol of formula IV in acidic aqueous medium, it is customary to use a wetting agent in order to expedite the coupling reaction in the heterogenous system. Sulfonate wetting agents such as sodium dodecylbenzene sulfonate, which are very soluble in water and which can be thus easily removed during isolation of the o-nitroazobenzene intermediate, are much preferred over the less water soluble non-ionic emulsifiers, such as Triton X-151, X-171 and X-800 available commercially from Rohm and Haas, which are more difficult to remove from the o-nitroazobenzene intermediate product of this coupling step. The presence of such latter emulsifiers in the o-nitroazobenzene intermediates tends to inhibit the subsequent reduction of the n-nitroazobenzene to the 2-aryl-2H-benzotriazole in the instant process.

The 2-aryl-2H-benzotriazoles have found wide use as dyestuff intermediates, optical brightener blue fluorescent agents and selective ultraviolet light absorbing stabilizers affording valuable protection for fibers, films and a variety of polymeric structures subject to deterioration by ultraviolet radiation. These materials have become important items of commerce.

The 2-aryl-2H-benzotriazoles are complex organic molecules which require careful synthetic procedures for their production in good yield and acceptable purity.

The present invention is concerned with an improved process to prepare ultraviolet stabilizers which are substituted 2-aryl-2H-benzotriazoles. These are distinguished by a very slight absorption in visible light and very high fastness to light in various substrates. Particularly valuable members of these stabilizers are compounds have a free hydroxyl group in the 2-position of the aryl group linked to the 2-nitrogen of the benzotriazole and which are further substituted in the 3- and 5- or the 4- and 5-positions by lower alkyl groups and may be substituted by a chlorine in the 5-position of the benzotriazole nucleus.

The description, preparation and uses of these valuable substituted 2-aryl-2H-benzotriazoles are further taught in the U.S. Pat. Nos. 3,004,896, 3,055,896, 3,072,585, 3,074,910, 3,189,615 and 3,230,194.

The following examples are given to illustrate the process of the present invention, but are not intended to limit the scope of the present invention in any manner whatsoever.

EXAMPLE 1

2-(2-Hydroxy-3,5-di-tert-amylphenyl)-2H-benzotriazole

To a 2000 ml. 3-necked, round-bottomed flask equipped with an agitator, reflux condenser, nitrogen inlet and thermometer were charged 155 grams of 2'-hydroxy-3',5'-di-tert-amyl-2-nitroazobenzene, 119 grams of isopropanol and 80 grams of Amsco mineral spirits. A stream of nitrogen was introduced over the surface of the contents of the flask and the nitrogen atmosphere was then maintained throughout the remainder of the reduction process. 13.7 grams of 50% aqueous sodium hydroxide solution and 222 grams of water were added and the temperature of the contents of the flask were adjusted to 55° C. The ratio of the moles of alkali to moles of o-nitroazobenzene intermediate used was 0.42/1. 104 grams of zinc dust was added in 5 portions over a 2 hour period with the temperature of the flask being held at 55°-60° C with some slight external cooling. The total concentration of iron impurities from all reactants totalled less than 150 ppm based on zinc used. After all the zinc was added, the temperature was raised to 60° C and held at this temperature until a spot test indicated no more o-nitroazobenzene intermediate was present. The temperature was then raised to 65° and held there for 4 to 5 hours or until TLC analysis indicated that no more of the N-oxy intermediate was present. 62.6 grams of anhydrous sodium sulfate and 35.6 grams of water were then added, the batch was heated to 70° C and stirred for 15 minutes. The material was then allowed to stand and separate into three liquid phases plus unreacted zinc dust. The top two layers containing the desired product were transferred to another flask. The remaining aqueous zinc slurry was washed at 65°-70° C with three successive 16 gram portions of Amsco mineral spirits: isopropanol 50:50. The combined product layers and wash liquids were then washed once at 70° C with an aqueous hydrochloric acid solution made from 130 grams of water and 40 grams of 32% hydrochloric acid to remove cleavage amine by-products. A second and third wash followed at 70° C with aqueous hydrochloric acid solutions made each from 65 grams of water and 20 grams of 32% hydrochloric acid. The last wash was essentially colorless. 14 grams of 32% hydrochloric acid and 220 grams of isopropanol were added to the solution of the product. The batch was allowed to crystallize slowly. The solid product form was filtered and washed with isopropanol at 0° C to give 110 grams of 2-(2-hydroxy-3,5-di-tert-amylphenyl)-2H-benzotriazole with a melting point of 80°-81° C. The yield was 77.5% of theory based on the o-nitroazobenzene intermediate.

The mother liquor from the first crop material isolated above was extracted with water to remove residual isopropanol. The Amsco mineral spirits were removed by distillation to give a residue which was then slurried with sufficient Amsco mineral spirits: isopropanol 50:50 to give an easily agitated slurry. The slurry was filtered at 0° C and the isolated solid was washed with isopropanol at 0° C to give 6 grams of a second crop of the product with a melting point of 79°-80° C. The second yield was 4% of theory.

A blend of the first and second crops of the product had a melting point of 80°-81° C. This combined blend also passed a stringent heat stability test for transmission after being held at 165° C for 4 hours.

The total yield of acceptable product was 116 grams or 81.5% of theory based on the o-nitroazobenzene intermediate.

EXAMPLE 2

Isolation of By-Product

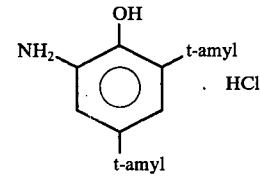

The aqueous hydrochloric acid wash solutions from Example 1 were partially neutralized to pH 5.5 with dilute alkali to yield an easily filterable slurry which was then filtered and dried. The grey solid was isolated in a yield of 2.3 grams of 2% of theory calculated as the hydrochloride salt of 2,4-di-tert-amyl-6-aminophenol.

When the molar ratio of sodium hydroxide to o-nitroazobenzene intermediate was increased to the range of 1.5-2.0 to 1 from the 0.42 to 1 ratio of Example 1, the yield of cleavage amine by-products rose to the undesirable 11.4% level.

TLC analysis of the solid material isolated in these runs indicated a main aminophenol spot with some minor impurities. Recrystallization of the solid from an isopropanol-hydrochloric acid mixture yielded the pure hydrochloride salt of 2,4-di-tert-amyl-6-aminophenol.

EXAMPLE 3

2-(2-Hydroxy-3,5-di-tert-amylphenyl)-2H-benzotriazole

The same procedure as described in Example 1 was carried out except that the 27.4 grams of 50% sodium hydroxide was used with 155 grams of 2'-hydroxy-3',5'-ditert-amyl-2-nitroazobenzene to give a ratio of moles of alkali to moles of o-nitroazobenzene intermediate of 0.048/1 compared to the ratio of 0.42/1 employed in Example 1.

More heat was involved in this case with the temperature of the reaction mixture rising momentarily to 73° C with normal external air cooling of the reaction flask.

Complete reduction was accomplished in 1.5 hours at 65° C.

The desired product was isolated in the manner described in Example 1, but the sodium sulfate charged was adjusted to give the same sodium ion concentration as in Example 1. 50.5 grams of anhydrous sodium sulfate and 30 grams of water were used in the first product isolation step.

The yield of first crop product was 109 grams, 76.7% of theory based on the o-nitroazobenzene intermediate. The product had acceptable heat stability properties.

The by-product material corresponding to that described in Example 2 was isolated in a 10 gram yield of 8.5% of theory, calculated as the hydrochloride salt of 2,4-tert-amyl-6-aminophenol.

The use of more alkali in this case compared to Example 1 decreased reaction time significantly, gave about the same yield of product, but significantly increased the yield of the undesired aminophenol by-product.

Example 3 represents about the upper limit of the range of the present invention in terms of balancing all factors of yield, reaction time and by-product formation for the reduction of o-nitroazobenzene intermediates of Type 1.

The amount of iron impurities in this Example was less than 150 ppm based on the zinc used.

EXAMPLE 4

2-(2-Hydroxy-3,5-di-tert-amylphenyl)-2H-benzotriazole

The exact procedure and amounts of reactants of Example 1 were used except that 0.03 grams of ferric oxide (a brown powder) was added to the reaction mixture just prior to addition of the zinc dust. The total amount of iron impurities in this system was 210 ppm based on the zinc used compared to a value less than 150 ppm in Example 1. The ratio of moles of alkali to moles of o-nitroazobenzene was 0.42/1 in both examples.

Complete reduction occurred in 5 hours at 65° C. Heat-stable product was isolated in a first crop yield of 96.0 grams, 67.6% of theory.

The amount of by-product isolated was 19.5 grams or 17% of theory calculated as 2,4-di-tert-amyl-6-aminophenol hydrochloride.

The presence of amounts of iron higher than 150 ppm based on zinc used clearly led to reduced yields of desired product and increased yields of cleavage amine by-product even at low alkali to o-nitroazobenzene ratios.

EXAMPLE 5

2-(2-Hydroxy-3,5-di-tert-amylphenyl)-2H-benzotriazole

When using the procedure of Example 4 the 0.03 grams of ferric oxide was replaced by 2.34 ml of 0.099N ferric chloride solution, the amount of iron impurities so added to the system were 80 ppm based on the zinc used.

The time for complete reduction to occur was 4 hours and the desired heat-stable product was obtained in a first crop yield of 94.5 grams, 66.5% of theory. The by-product was isolated in a yield of 18% of theory calculated as 2,4-di-tert-amyl-6-aminophenyl hydrochloride.

The yields of product and by-product were essentially the same in both Examples 4 and 5 although far less ferric chloride was added to achieve the same results. This difference is believed due to the physical state (size of particle, dispersibility, and the like) of the iron impurities involved. It is clear that, when the iron is very finely dispersed, it took much less of it to effect detrimentally the yields of the present invention.

The ratio of moles of alkali to moles of o-nitroazobenzene intermediate was 0.42/1 in this case.

EXAMPLE 6

2-(2-Hydroxy-3,5-di-tert-anylphenyl)-2H-benzotriazole

When using the procedure and quantities of materials described in Example 1, the total amount of iron impurities in the reaction system based on the zinc used was less than 35 ppm, excellent results in terms of reaction time, high yield of heat-stable, first crop reaction product and low yields of undesired cleavage amine by-products were obtained.

Complete reduction occurred at 65° C in 2.75 hours and the yield of heat-stable, first crop product was 118 grams, 83% of theory based on the o-nitroazobenzene intermediate. The yield of the undesired by-product calculated as 2,4-di-tert-amyl-6-aminophenol hydrochloride was only 3% of theory.

The ratio of moles of alkali to moles of o-nitroazobenzene intermediate was 0.42/1 in this case. This, coupled with the low iron impurity content, represents a preferred embodiment of the invention.

EXAMPLE 7

5-Chloro-2-(2-hydroxy-3,5-di-tert-butylphenyl)-2H-benzotriazole

When in Example 1, the 2'-hydroxy-3',5'-di-tert-amyl-2-nitroazobenzene was replaced by an equivalent amount of 2'-hydroxy-3',5'-di-tert-butyl-5-chloro-2-nitroazobenzene, the product 5-chloro-2-(2-hydroxy-3,5-di-tert-butylphenyl)-2H-benzotriazole was obtained after a reaction time o 5 hours in a yield of 80.4% of theory as an isolated product of melting point 151°–154° C. An additional 4.5% yield was present in the mother liquor for an overall yield of 84.9% of theory.

EXAMPLE 8

5-Chloro-2-(2-hydroxy-3,5-di-tert-butylphenyl)-2H-benzotriazole

When in Example 7 the 0.42 moles of sodium hydroxide per mole of o-nitroazobenzene intermediate was replaced by 0.8 moles of sodium hydroxide per mole of o-nitroazobenzene intermediate and with a reaction time of 2 hours, the product 5-chloro-2-(2-hydroxy-3,5-di-tert-butylphenyl)-2H-benzotriazole was obtained in an isolated yield of 86.1% with a melting point of 152°–155° C. An additional 1.1% yield was present in the mother liquor for an overall yield of 87.2% of theory.

EXAMPLE 9

2-(2-Hydroxy-3-methyl-5-tert-butylphenyl)-2H-benzotriazole

When in Example 1, the 2'-hydroxy-3',5'-di-tert-amyl-2-nitroazobenzene was replaced by an equivalent amount of 2'-hydroxy-3'-methyl-5'-tert-butyl-2-nitroazobenzene, the product 2-(2-hydroxy-3-methyl-5-tert-butylphenyl)-2H-benzotriazole was obtained after a reaction time of 5 hours in an isolated yield of 81% of theory with a melting point of 145°-146° C.

EXAMPLE 10

5-Chloro-2(2-hydroxy-3-tert-butyl-5-methylphenyl)-2H-benzotriazole

When in Example 1, the 2'-hydroxy-3',5'-di-tert-amyl-2-nitroazobenzene is replaced by an equivalent amount of 2'-hydroxy-3'-tert-butyl-5'-methyl-5-chloro-2-nitroazobenzene and the ratio of the moles of alkali to moles of o-nitroazobenzene intermediate is 0.848/1, the product 5-chloro-2-(2-hydroxy-3-tert-butyl-5-methylphenyl)-2H-benzotriazole is obtained.

EXAMPLE 11

2-(2-Hydroxy-3-(α-methylbenzyl)-5-methylphenyl)-2H-benzotriazole

When in Example 1, the 2'hydroxy-3',5'-di-tert-amyl-2-nitroazobenzene is replaced by an equivalent amount of 2'-hydroxy-3'-(α-methylbenzyl)-5'-methyl-2-nitroazobenzene, the product 2-(2-hydroxy-3-(α-methylbenzyl)-5-methylphenyl)-2H-benzotriazole is obtained.

EXAMPLE 12

2-(2Hydroxy-5-methylphenyl)-2H-benzotriazole

To a 2000 ml bottom outlet flask equipped with an agitator, reflux condenser, nitrogen inlet and thermometer was charged 143.7 grams of 2'-hydroxy-5'-methyl-2-nitroazobenzene (95% purity) followed by 280 ml of toluene. The agitator was started at medium speed and 298 grams of water was then added followed by 54 grams of a 50% sodium hydroxide solution. The ratio of moles of sodium hydroxide to moles of o-nitroazobenzene intermediate was 1.2/1. A stream of nitrogen was maintained over the surface of the reaction mixture throughout the remainder of the reaction. In order to saturate the system, some 14.3 grams of previously prepared desired product 2-(2-hydroxy-5-methylphenyl)-2H-benzotriazole was added and the temperature of the contents of the flask was adjusted to 45°-50° C. To the reddish stirred reaction mixture was added 107 grams of zinc dust in 5 portions over a 2-hour period with the temperature of the reaction mixture being held at 45°-50° C throughout with some slight external cooling. The total concentration of iron impurities from all reactants totalled less than 150 ppm based on zinc used. After all of the zinc was charged, the temperature was increased to 55° C and held for 3 to 4 hours or until TLC analysis indicated that no more N-oxy intermediate was present.

The temperature of the reaction mixture was raised to 70°-75° C and 18.2 grams of sodium sulfate was added. The batch was moderately agitated for 15 minutes at 70°-75° C and then allowed to separate into three liquid phases plus unreacted zinc dust. The aqueous zinc layer was split off and saved for recovery. The temperature of the product layers was increased to 75°-80° C and a solution of 31% sulfuric acid made from 41.2 grams of 70% sulfuric acid and 80 grams of water was added. The reaction mixture was stirred slowly for 15 minutes and then allowed to separate into layers. The dark sulfuric acid layer was separated off. The product layer was again extracted with 59.7 grams of 70% sulfuric acid and finally with 29.9 grams of 70% sulfuric acid.

The toluene solution of the desired product was held at 75°-80° C with moderate stirring, treated with 7.5 grams of Filtrol Special Grade No. 4 for 15 minutes and then filtered. The reaction flask was rinsed with 200 ml of toluene which was combined with the product solution. The product solution was cooled with stirring and the desired product began crystallizing out of solution at 45°-50° C. The desired product was isolated by filtration, washed with 50 ml of cold isopropanol and vacuum dried at 45°-50° C to give 93.7 grams of 2-(2-hydroxy-5-methylphenyl)-2H-benzotriazole with a melting point of 126°-129° C. The yield was 78.5% of theory based on the o-nitroazobenzene intermediate.

The mother liquor contained another 17.2 grams of product or a net amount of 2.9 grams or an additional 2.4% yield. The overall yield of product was 80.9%.

EXAMPLE 13

2-(2-Hydroxy-5-methylphenyl)-2H-benzotriazole

When in Example 1, the 2'-hydroxy-3',5'-di-tert-amyl-2-nitroazobenzene was replaced by an equivalent amount of 2'-hydroxy-5'-methyl-2-nitroazobenzene and the mole ratio of sodium hydroxide to o-nitroazobenzene intermediate was increased from 0.42/1 to 1.26/1, the reaction went rapidly to yield the product 2-(2-hydroxy-5-methylphenyl)-2H-benzotriazole.

EXAMPLE 14

2-(2-Hydroxy-5-tert-butylphenyl)-2H-benzotriazole

When in Example 13, the 2'-hydroxy-5'-methyl-2-nitroazobenzene was replaced by an equivalent amount of 2'-hydroxy-5'-tert-butyl-2-nitroazobenzene, the reduction reaction went rapidly to yield the product 2-(2-hydroxy-5-tert-butylphenyl)-2H-benzotriazole.

EXAMPLE 15

2-(2-Hydroxy-5-tert-octylphenyl)-2H-benzotriazole

When in Example 1, the 2'-hydroxy-3',5'-di-tert-amyl-2-nitroazobenzene was replaced by an equivalent amount of 2'-hydroxy-5'-tert-octyl-2-nitroazobenzene and the moles of sodium hydroxide per mole of o-nitroazobenzene intermediate was increased from 0.42/1 to 1.2/1, the product 2-(2-hydroxy-5-tert-octylphenyl)-2H-benzotriazole was obtained in an isolated yield of 62.6% of theory with a melting point of 104°-107° C. The mother liquor contained a compound believed to be an isomer of the desired product.

What is claimed is:

1. An improved process for the production of 2-aryl-2H-benzotriazoles of the formula I

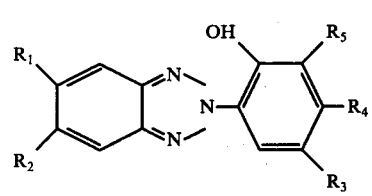

wherein
$R_1$ is hydrogen,
$R_2$ is hydrogen or chlorine,
$R_3$ is methyl, sec-butyl, tert-butyl, tert-amyl, tert-octyl, cyclohexyl, chlorine or carboxyethyl,
$R_4$ is hydrogen, and
$R_5$ is chlorine, methyl, tert-butyl, sec-butyl, tert-amyl, tert-octyl or α-methylbenzyl by the reduction at a temperature between about 55° to about 73° C of the corresponding o-nitroazobenzene intermediate

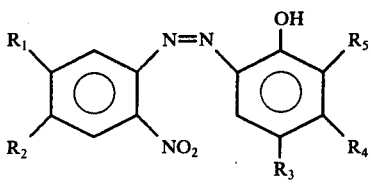

by adding zinc to an aqueous alkali metal hydroxide medium containing said o-nitroazobenzene intermediate wherein the improvement comprises
  employing an initial ratio of moles of alkali to moles of o-nitroazobenzene intermediate in the range of 0.2 to 0.848/1 in the presence of an amount of iron impurities in the reaction system of less than 150 ppm based on zinc used, and with no additional alkali or o-nitroazobenzene being added during the reduction reaction.

2. The process according to claim 1 wherein the ratio of moles of alkali to moles of o-nitroazobenzene intermediate is 0.3–0.7/1 in the presence of an amount of iron impurities in the reaction system less than 100 ppm based on zinc used.

3. The process according to claim 1 wherein the ratio of moles of alkali to moles of o-nitroazo intermediate is 0.3–0.6/1 in the presence of an amount of iron impurities in the reaction system of less than 50 ppm based on zinc used.

4. The process according to claim 1 further comprising
  carrying out the reduction reaction in an aqueous polar/non-polar solvent mixture.

5. The process according to claim 4 wherein the polar/non-polar solvent mixture is aqueous isopropanol/mineral spirits.

6. The process according to claim 1 for the production of 2-(2-hydroxy-3,5-di-tert-amylphenyl)-2H-benzotriazole.

7. The process according to claim 1 for the production of 5-chloro-2(2-hydroxy-3,5-di-tert-butylphenyl-2H-benzotriazole.

8. The process according to claim 1 for the production of 5-chloro-2-(2-hydroxy-3-tert-butyl-5-methylphenyl)-2H-benzotriazole.

9. The process according to claim 1 for the production of 2-(2-hydroxy-3-(α-methylbenzyl)-5-methylphenyl)-2H-benzotriazole.

10. An improved process for the production of 2-aryl-2H-benzotriazoles of the formula I

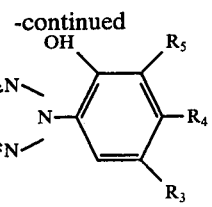

(I)

-continued

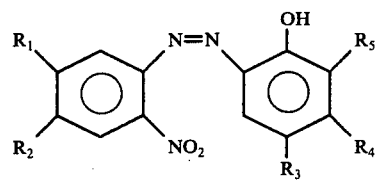

wherein
  $R_1$ is hydrogen,
  $R_2$ is hydrogen or chlorine,
  $R_3$ is metyl, sec-butyl, tert-butyl, tert-amyl, tert-octyl, cyclohexyl, chlorine or carboxyethyl,
  $R_4$ is hydrogen, and
  $R_5$ is hydrogen
  by the reduction at a temperature between about 45° and 75° C of the corresponding o-nitroazobenzene intermediate

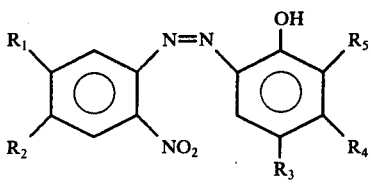

by adding zinc to an aqueous alkali metal hydroxide medium containing said o-nitroazobenzene intermediate wherein the improvement comprises
  employing an initial ratio of moles of alkali to moles of o-nitroazobenzene intermediate in the range of 1.2 to 1.7/1 in the presence of an amount of iron impurities in the reaction system of less than 150 ppm based on zinc used, and with no additional alkali or o-nitroazobenzene being added during the reduction reaction.

11. The process according to claim 10 wherein the ratio of moles of alkali to moles of o-nitroazobenzene intermediate is 1.2–1.4/1 in the presence of an amount of iron impurities in the reaction system less than 100 ppm based on zinc used.

12. The process according to claim 10 wherein the ratio of moles of alkali to moles of o-nitroazo intermediate is 1.2 to 1.3/1 in the presence of an amount of iron impurities in the reaction system of less than 50 ppm based on zinc used.

13. The process according to claim 10 further comprising
  carrying out the reduction reaction in an aqueous-/aromatic solvent mixture.

14. The process according to claim 13 wherein the aromatic solvent is toluene.

15. The process according to claim 10 for the production of 2-(2-hydroxy-5-methylphenyl)-2H-benzotriazole.

16. The process according to claim 10 for the production of 2-(2-hydroxy-5-tert-octylphenyl)-2H-benzotriazole.

* * * * *